(12) United States Patent
Foster

(10) Patent No.: US 7,597,198 B1
(45) Date of Patent: Oct. 6, 2009

(54) NOVELTY KIT

(76) Inventor: John D. Foster, 5431 Michael Way, Sacramento, CA (US) 95822

( * ) Notice: Subject to any disclaimer, the term of this patent is extended or adjusted under 35 U.S.C. 154(b) by 540 days.

(21) Appl. No.: 11/350,362

(22) Filed: Feb. 9, 2006

(51) Int. Cl.
*B65D 73/00* (2006.01)
(52) U.S. Cl. ........................... 206/575; 206/457
(58) Field of Classification Search ............ 206/459.1, 206/457, 581, 225, 233, 575
See application file for complete search history.

(56) References Cited

U.S. PATENT DOCUMENTS

| 4,024,880 | A | | 5/1977 | Newton et al. | |
|---|---|---|---|---|---|
| 4,177,593 | A | * | 12/1979 | Lockey | 40/488 |
| 4,321,998 | A | * | 3/1982 | Van de Walker et al. | 206/229 |
| 4,899,882 | A | * | 2/1990 | Benner | 206/470 |
| 4,916,758 | A | | 4/1990 | Jordan-Ross | |
| 5,035,324 | A | * | 7/1991 | Bertrand | 206/457 |
| 5,193,675 | A | | 3/1993 | Otis | |
| 5,383,891 | A | | 1/1995 | Walker | |
| 5,447,227 | A | | 9/1995 | Kosberg | |
| 5,718,336 | A | * | 2/1998 | Haarlander | 206/542 |
| 5,806,678 | A | * | 9/1998 | Håkansson | 206/438 |
| 5,826,714 | A | | 10/1998 | Martin | |
| 5,908,108 | A | | 6/1999 | Svopa | |
| 5,967,307 | A | * | 10/1999 | Wang | 206/217 |
| 6,021,902 | A | * | 2/2000 | Wu | 206/534 |

* cited by examiner

*Primary Examiner*—Jacob K Ackun, Jr.

(57) ABSTRACT

A novelty kit for provide supplies and to amuse a caregiver expecting a baby includes a container including a bottom wall and a perimeter wall being attached to and extending upwardly from the bottom wall. The perimeter wall has an upper edge defining an opening extending into an interior space of the container. Humorous indicia are positioned on an outer surface of said container. A cover is attached to the upper edge of the container. The cover is selectively positionable in a closed position extending over said opening.

1 Claim, 2 Drawing Sheets

NOVELTY KIT

BACKGROUND OF THE INVENTION

1. Field of the Invention

The present invention relates to gift kits and more particularly pertains to a new gift kit for provide supplies and to amuse a caregiver expecting a baby.

2. Description of the Prior Art

The use of gift kits is known in the prior art. U.S. Pat. No. 4,024,880 describes a system for assisting and amusing the owner who recently received on infant pet. Another type of gift kit is U.S. Pat. No. 5,908,108 for providing an expectant father with a plurality of useful items.

While these devices fulfill their respective, particular objectives and requirements, the need remains for a system that has certain improved features that amuse an expectant caregiver and provide items that the expectant caregiver may find useful once a baby has arrived.

SUMMARY OF THE INVENTION

The present invention meets the needs presented above by generally comprising a container including a bottom wall and a perimeter wall being attached to and extending upwardly from the bottom wall. The perimeter wall has an upper edge defining an opening extending into an interior space of the container. Humorous indicia are positioned on an outer surface of said container. A cover is attached to the upper edge of the container. The cover is selectively positionable in a closed position extending over said opening.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 2:
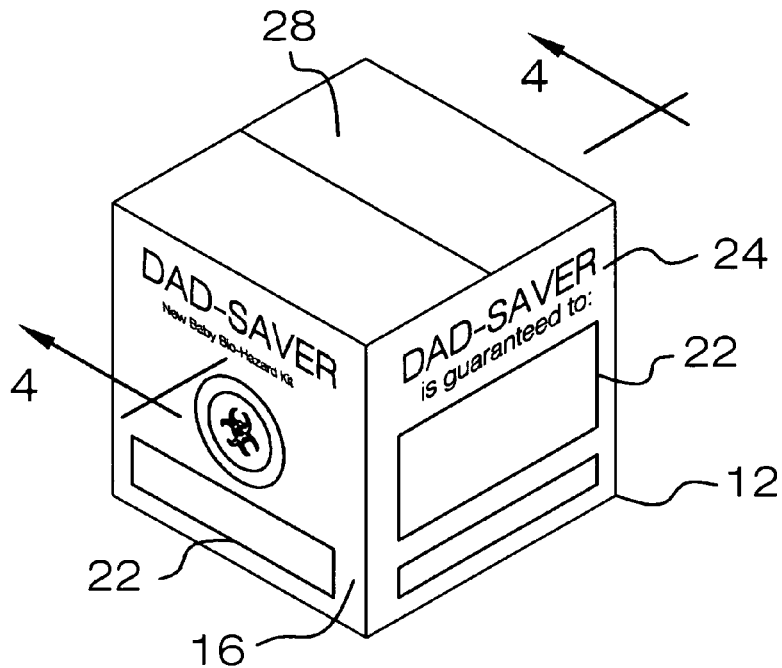
FIG. 2 is a perspective view of the present invention with the cover positioned over the opening.
Figure 1:
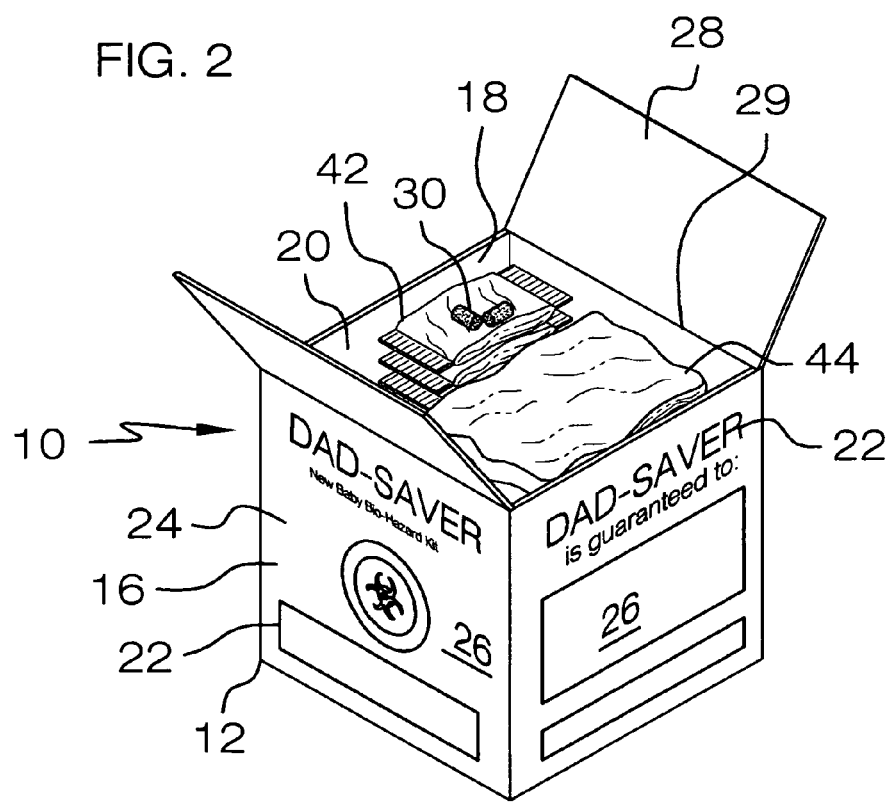
FIG. 1 is a perspective view of a novelty kit according to the present invention.
Figure 3:
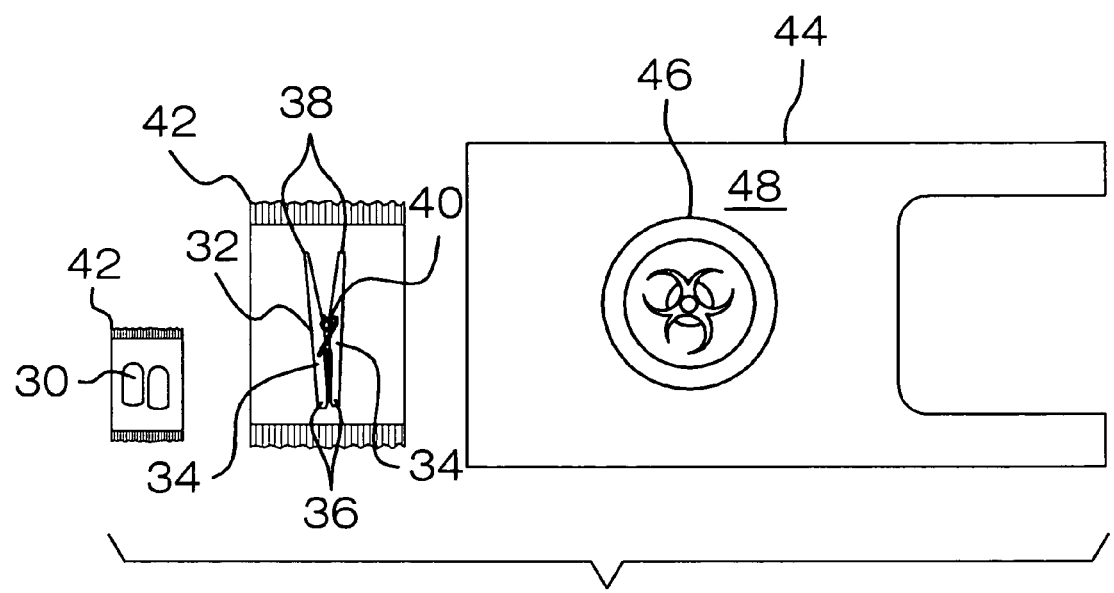
FIG. 3 is a top view of the pouches, disposal bag, earplugs and clip of the present invention.
Figure 4:
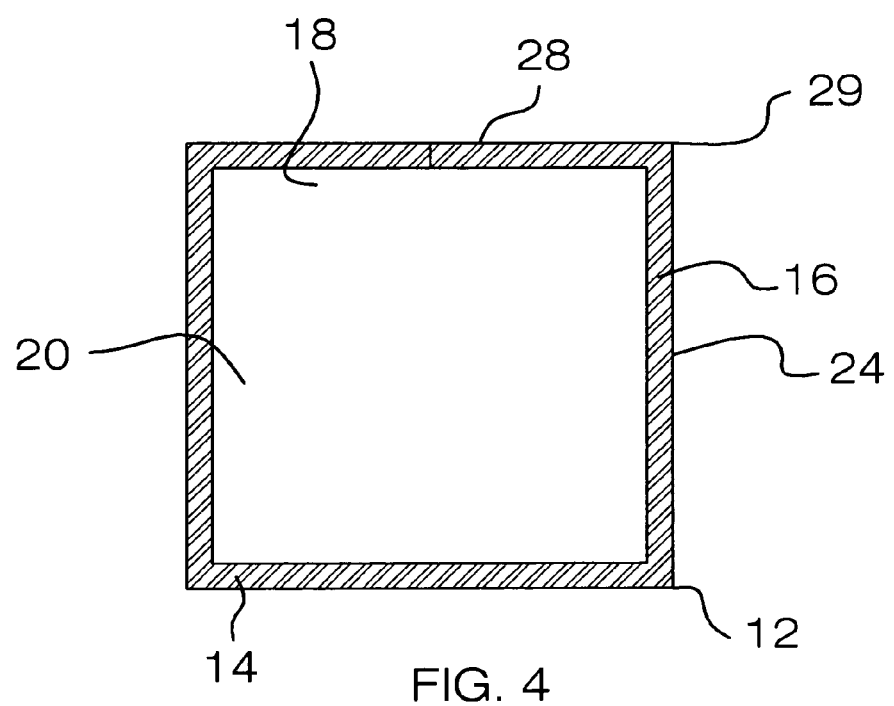
FIG. 4 is a cross-sectional view of the container of the present invention taken along line 4-4 of FIG. 2.

With reference now to the drawings, and in particular to FIGS. 1 through 4 thereof, a new gift kit embodying the principles and concepts of the present invention and generally designated by the reference numeral 10 will be described.

As best illustrated in FIGS. 1 through 4, the novelty kit 10 generally comprises a container 12 including a bottom wall 14 and a perimeter wall 16 being attached to and extending upwardly from the bottom wall 14. The perimeter wall 16 has an upper edge 29 defining an opening 18 extending into an interior space 20 of the container 12. Humorous indicia 22 are positioned on an outer surface 24 of the container 12. The outer surface 24 includes a plurality of exterior faces 26. At least two of the exterior faces 26 having the humorous indicia 22 are positioned thereon. The humorous indicia 22 indicates humorous situations of a caregiver caring for an infant. A cover 28 is attached to the upper edge 29 of the container 12. The cover 28 is selectively positionable in a closed position extending over the opening 18.

At least one pair of earplugs 30 is provided. The earplugs 30 are each configured to be insertable into ears of the caregiver to dampen surrounding ambient sounds. The earplugs 30 are removably positioned in the interior space 20. At least one clip 32 is configured to engage a nose of the caregiver to selectively close the nostrils of the caregiver and inhibit the caregiver from smelling unpleasant aromas. The clip 32 is removably positioned in the interior space 20. The at least one clip 32 includes a pair of arms 34 each having a first end 36 and a second end 38. A biasing member 40 is coupled to the arms 34 to bias the first end 36s of the arms 34 together on a nose of the caregiver. The second ends 38 are pushed together by the caregiver to force the first ends 36 of the arms 34 apart to facilitate insertion and removal of the nose from the at least one clip 32. A plurality of pouches 42 each containing one of the at least one pair of earplugs 30 and the at least one clip 32. Each of the pouches 42 is easily torn to gain access inside the pouches 42.

At least one disposal bag 44 is configured to receive a soiled diaper from a baby to permit the soiled diaper to be contained in the at least one disposal bag 44 and facilitate disposal of the soiled diaper. Warning indicia 46 on an exterior surface 48 of the at least one disposal bag 44 indicates disgusting contents of the soiled diaper.

In use, the caregiver opens the container 12 and removes and tears open one of the pouches 42 containing the at least one pair of earplugs 30. The caregiver may then insert the pair of earplugs 30 into the ears of the caregiver to dampen ambient sounds such as a baby crying or a spouse's voice. When it is time to change a baby's diaper the caregiver removes and tears open one of the pouches 42 containing the at least one clip 32 and clip 32s the at least one clip 32 to the nose of the caregiver to inhibit smelling the contents of the diaper. The diaper once removed from the baby is then placed in the at least one disposal bag 44. The at least one disposal bag 44 is then tied closed and then thrown away with the diaper inside the at least one disposal bag 44.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A novelty kit for presenting to a caregiver of an infant, said novelty kit comprising:

a container including a bottom wall and a perimeter wall being attached to and extending upwardly from said bottom wall, said perimeter wall having an upper edge defining an opening extending into an interior space of said container;

humorous indicia being positioned on an outer surface of said container, said outer surface including a plurality of exterior faces, at least two of said exterior faces having said humorous indicia being positioned thereon;

a cover being attached to said upper edge of said container, said cover being selectively positionable in a closed position extending over said opening;

at least one pair of earplugs being configured to be inserted into ears of the caregiver to dampen surrounding ambient sounds, said earplugs being removably positioned in said interior space;

at least one clip being configured to engage a nose of the caregiver to selectively close the nostrils of the caregiver and inhibit the caregiver from smelling unpleasant aromas, said clip being removably positioned in said interior space, said at least one clip including a pair of arms each having a first end and a second end, a biasing member being coupled to said arms to bias said first ends of said arms together on a nose of the caregiver, said second ends being pushed together by the caregiver to force said first ends of said arms apart to facilitate insertion and removal of the nose from the at least one clip;

a plurality of pouches, each of said pouches containing one of said at least one pair of earplugs and said at least one clip, each of said pouches being easily torn to gain access inside said pouches;

at least one disposal bag being configured to receive a soiled diaper from a baby; and warning indicia on an exterior surface of said at least one disposal bag to indicate disgusting contents of the soiled diaper.

* * * * *